United States Patent [19]

Acker et al.

[11] 4,360,517
[45] Nov. 23, 1982

[54] N-METHYL-N-SILYL-CARBAMATES AND THEIR USE FOR COMBATING PESTS

[75] Inventors: Rolf-Dieter Acker, Leimen; Gerhard Hamprecht, Weinheim; Karl Kiehs, Lampertheim; Heinrich Adolphi, Limburgerhof, all of Fed. Rep. of Germany

[73] Assignee: BASF Aktiengesellschaft, Fed. Rep. of Germany

[21] Appl. No.: 221,832

[22] Filed: Dec. 31, 1980

[30] Foreign Application Priority Data

Jan. 25, 1980 [DE] Fed. Rep. of Germany ....... 3002603

[51] Int. Cl.³ .............................................. A01N 55/00
[52] U.S. Cl. .................................... 424/184; 556/411
[58] Field of Search ......................... 556/411; 424/184

[56] References Cited

U.S. PATENT DOCUMENTS 2,903,478  9/1959  Lambrech .
3,962,316  6/1976  Kiehs et al. .

OTHER PUBLICATIONS

Fahmy et al., Jour. Agr. & Food Chem., vol. 14 (1966), pp. 79–83.

Primary Examiner—Bernard Helfin
Attorney, Agent, or Firm—Keil & Witherspoon

[57] ABSTRACT

N-Methyl-N-silyl-carbamates of the formula

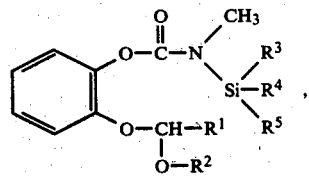

where $R^1$ denotes hydrogen or unsubstituted or halogen-substituted alkyl of a maximum of 4 carbon atoms, $R^2$, $R^3$ and $R^4$ are identical or different and each denotes alkyl of a maximum of 4 carbon atoms, and $R^5$ denotes alkyl of a maximum of 4 carbon atoms or phenyl, processes for their manufacture, and their use for combating pests.

7 Claims, No Drawings

N-METHYL-N-SILYL-CARBAMATES AND THEIR USE FOR COMBATING PESTS

The present invention relates to N-methyl-N-silyl-carbamates, pesticides containing these carbamates as active ingredients, and a process for combating pests with these compounds.

It has been disclosed that aryl-N-methyl-carbamates are suitable for combating pests. They are effective on biting and sucking insects and on spider mites (German Laid-Open Application DE-OS 2,231,249 and U.S. Pat. No. 2,903,478).

We have found that N-methyl-N-silyl-carbamates of the formula

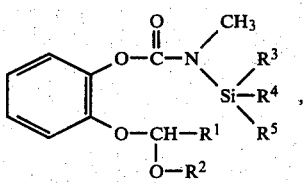

where $R^1$ denotes hydrogen or unsubstituted or halogen-substituted alkyl of a maximum of 4 carbon atoms, $R^2$, $R^3$ and $R^4$ are identical or different and each denotes alkyl of a maximum of 4 carbon atoms, and $R^5$ denotes alkyl of a maximum of 4 carbon atoms or phenyl, have a pesticidal action, particularly an insecticidal action, which is superior to that of prior art aryl-N-methyl-carbamates. The toxicity to warmbloods of the N-methyl-N-silyl-carbamates is less than that of the corresponding non-silylated carbamates. The warmblood toxicity of 2-(1-methoxy-2-chloroethoxy)-phenyl-N-methyl-N-trimethylsilyl-carbamate, for example, is 3 times less than that of 2-(1-methoxy-2-chloroethoxy)-phenyl-N-methyl-carbamate.

Substituents $R^2$, $R^3$, $R^4$ and $R^5$ in formula I denote linear or branched alkyl of a maximum of 4 carbon atoms, such as methyl, ethyl, n-propyl, isopropyl, n-butyl, tert-butyl and isobutyl. $R^5$ may also denote phenyl. $R^1$ may denote halogen-substituted alkyl of a maximum of 4 carbon atoms, such as chloromethyl, bromomethyl, iodomethyl, 1-chloroethyl, 2-chloroethyl, 1-bromoethyl and 2-bromoethyl.

The N-methyl-N-silyl-carbamates of the formula I may be obtained by reaction of a carbamate of the formula

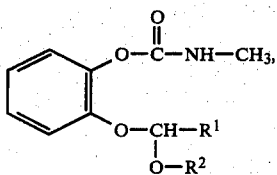

where $R^1$ and $R^2$ have the above meanings, with a halosilane of the formula

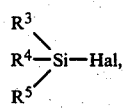

where $R^3$, $R^4$ and $R^5$ have the above meanings and Hal denotes halogen, in the presence or absence of a solvent and/or in the presence of an acid binder.

Examples of acid binders are alkali metals, alkali metal hydrides, alkali metal and alkaline earth metal hydroxides, carbonates and bicarbonates, organometallic compounds and tertiary organic amines. Particularly suitable examples are lithium, lithium hydride, sodium hydride, potassium hydride, calcium hydride, phenyl lithium, n-butyl lithium, methyl lithium, sodium methylate, magnesium methylate, methyl magnesium bromide, ethyl magnesium bromide, phenyl magnesium bromide, phenyl magnesium chloride, potassium methylate, sodium propylate, aluminum isopropylate, sodium butylate, lithium methylate, calcium cyclohexanoate, sodium propylate, potassium tert-butylate, trimethylamine, triethylamine, tri-n-propylamine, triisopropylamine, tributylamine, triisobutylamine, tri-sec-butylamine, tri-tert-butylamine, tribenzylamine, tricyclohexylamine, triamylamine, trihexylamine, N,N-dimethylaniline, N,N-diethylaniline, N,N-diisopropylaniline, N,N-dimethyltoluidine, N,N-diethyltoluidine, N,N-dipropyltoluidine, 4-N,N-dimethylamino-pyridine, 4-N,N-diethylaminopyridine, N-methylpiperidine, N-ethylpiperidine, N-methylpyrrolidine, N-ethylpyrrolidine, N-methylpyrrole, N-methylmorpholine, N-ethylmorpholine, N-methylhexamethylenimine, pyridine, quinoline, α-,β- and γ-picoline, acridine, N,N,N',N'-tetramethylethylenediamine, N-ethyldiisopropylamine and N,N-dimethylcyclohexylamine. However, other basic compounds which are conventionally used may also be employed.

It may be advantageous to carry out the reaction in the presence of a reaction accelerator usually used for silylation reactions. Imidazole and 4-dimethylaminopyridine are suitable examples.

The reaction is generally carried out at from −40° to +100° C., preferably from −40° to +80° C., for from 30 minutes to 200 hours, preferably from 1 to 20 hours, at atmospheric or superatmospheric pressure, and batchwise or continuously.

Generally, to manufacture the silyl-carbamates of the formula I, from 0.5 to 2 moles, preferably from 0.9 to 1.5 moles, of the compound of the formula III and, if used, from 0.5 to 2 moles, preferably from 0.9 to 1.5 moles, of acid binder are employed per mole of the compound of the formula II. If the acid binder is an alkali metal, an alkali metal hydride, or an alkali metal or alkaline earth metal alcoholate, the carbamate of the formula II may first be converted into its alkali metal or alkaline earth metal salt and then employed in this form.

In a preferred embodiment, the acid acceptor is added in portions to a solution of the carbamate and the halotrialkylsilane in a suitable solvent; however, the portionwise addition of the starting materials to the acid binder is also possible.

For economic reasons, chlorides are preferred as compounds of the formula III. However, bromides, iodides and fluorides may also be used. The compounds of the formula III may be prepared by the methods described in Organosilicon Compounds, pp. 167-193, Academic Press, Inc., New York, 1960. The carbamates of the formula II are known.

The N-methyl-N-silyl-carbamates of the formula I may also be prepared by reaction of carbamates of the formula II with a silyl transfer agent of the formula

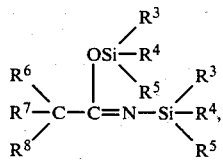

where $R^3$, $R^4$ and $R^5$ have the above meanings and $R^6$, $R^7$ and $R^8$ independently of each other denote hydrogen, halogen or alkyl of a maximum of 4 carbon atoms. The reaction is carried out in an inert solvent, if desired with the addition of a reaction accelerator.

If 2-isopropoxyphenyl-N-methyl-carbamate is reacted with N,O-bis-trimethylsilyl-trifluoroacetamide in the presence of trimethylchlorosilane as reaction accelerator, the reaction may be represented as follows:

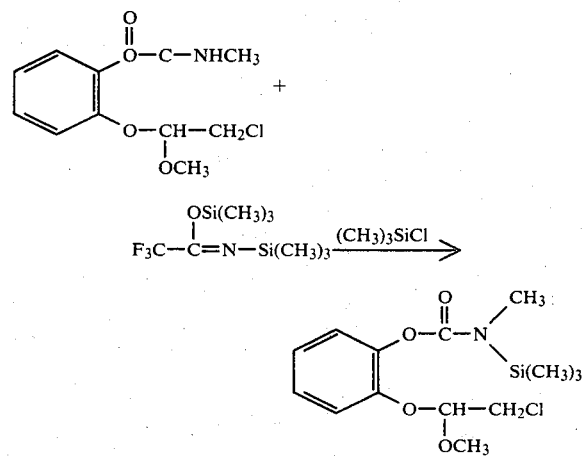

In this process for the manufacture of the carbamates of the formula I, generally from 0.5 to 2 moles, preferably from 0.9 to 1.3 moles, of the silylation agent of the formula IV is used per mole of the compound of the formula II. The components may be added in any order. The pressure is not critical; for simplicity's sake, atmospheric pressure is preferred.

The process is generally carried out at from −40° to +100° C., preferably from −40° to +80° C., and for from 30 minutes to 200 hours, preferably from 1 to 20 hours.

Examples of suitable reaction accelerators are trialkylchlorosilanes of the formula III, such as trimethylchlorosilane. Advantageously, from 0.5 to 10 mole% of reaction accelerator, based on the trialkylsilyl transfer agent of the formula IV, is used.

The compounds of the formula IV and the manufacture thereof are described in Pierce, A.E., Silylation of Organic Compounds, Pierce Chem. Comp., Rockford, Ill., 1968.

For both processes for the manufacture of the N-methyl-N-silyl-carbamates of the formula I, for example the following inert diluents may be used: formamides, such as dimethylformamide and dimethylacetamide; nitriles, such as acetonitrile, benzonitrile and butyronitrile; sulfoxides, such as dimethyl sulfoxide; phosphoramides, such as hexamethylphosphoric triamide; ketones, such as acetone, ethyl methyl ketone, cyclohexanone and acetophenone; ethers, such as tetrahydrofuran, anisole, dimethyloxyethane, n-butyl ethyl ether and dioxane; nitroalkanes, such as nitromethane; nitrobenzene; ureas, such as tetramethylurea; sulfones, such as sulfolane; esters, such as methyl acetate, methyl propionate, and methyl formate; halohydrocarbons, especially chlorohydrocarbons, e.g., methylene chloride, chloroform, 1,2-dichloroethane, 1,1,2,2- or 1,1,1,2-tetrachloroethane, dichloropropane, trichloroethylene, chlorobenzene, o-, m- and p-dichlorobenzene, fluorobenzene, o-, m- and p-chlorotoluene, dichloronaphthalene and carbon tetrachloride; aliphatic or cycloaliphatic hydrocarbons, such as heptane, pinane, gasoline fractions in the 70° to 190° C., boiling point range, cyclohexane, methylcyclohexane, decalin, petroleum ether, ligroin, 2,2,4-trimethylpentane and octane; aromatic hydrocarbons, such as benzene, toluene, o-, m- and p-cymene, o-, m- and p-xylene and tetrahydronaphthalene; and mixtures thereof. The solvent is advantageously employed in an amount of from 100 to 2,000 wt%, preferably from 100 to 1,000 wt%, based on the starting compound of the formula II.

To avoid silyl chloride losses by hydrolysis, it is advisable to carry out the reaction in a protective atmosphere, e.g., under nitrogen or argon.

The end products of the formula I may be isolated by filtering off undissolved matter and concentrating the solution. If further purification is desired, the products may be taken up in solvents, e.g., pentane, petroleum ether or cyclohexane, the solvent being removed under reduced pressure after renewed filtration. Purification by chromatography is also possible.

The compounds according to the invention may also be prepared in accordance with the following scheme:

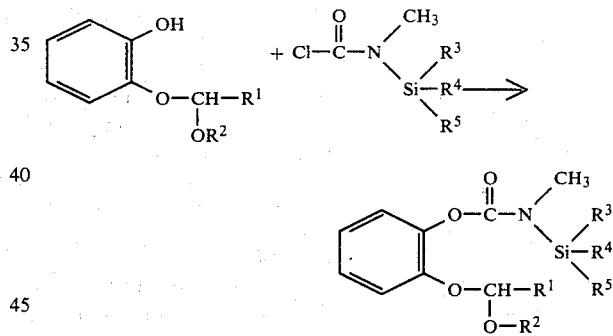

The substituents $R^1$, $R^2$, $R^3$, $R^4$ and $R^5$ have the above meanings.

Transsilylations may also be carried out with other conventional silylation reagents, e.g., hexamethyldisilazane, N-trialkylsilyldialkylamines and N-trialkylsilylcarboxamides.

The following examples, in which parts are by weight, illustrate the preparation of the N-methyl-N-silyl-carbamates of the formula I.

EXAMPLE 1

5.2 g parts of 2-(1-methoxy-2-chloroethoxy)-phenyl-N-methylcarbamate is dissolved in 25 parts of tetrahydrofuran. Under a nitrogen blanket, 3.1 parts of trimethylchlorosilane is added at 0° C., 2.6 parts of triethylamine is dripped in in portions, and the mixture is kept for an hour at room temperature and then stirred for 6 hours at from 40° to 50° C. After the mixture has cooled and undissolved matter has been filtered off, the solution is concentrated, taken up in cyclohexane and again concentrated. There is obtained 3.9 parts of 2-(1- methoxy-2-chloroethoxy)-phenyl-N-methyl-N-trimethylsilyl-carbamate (active ingredient no. 1); $n_D^{22} = 1.5000$.

NMR ($\delta$ in ppm): 0.30 (s, 9H, Si(CH$_3$)$_3$); 2.8–3.0 (m, 3H, CH$_3$); 3.40 (s, 3H, OCH$_3$); 3.4–3.8 (m, 2H, CH$_2$); 5.1–5.3 (m, 1H, cH), 6.8–7.3 (m, 4H, aromatic).

EXAMPLE 2

4.67 parts of 2-(1-methoxy-2-chloroethoxy)-phenyl-N-methylcarbamate is dissolved in 15 parts of acetonitrile. 4.64 parts of N,O-bis-trimethylsilyl-trifluoroacetamide and 0.1 part of trimethylchlorosilane are then added one after the other. The mixture is kept for 2 hours at 40° C. and then stirred for a further 2 hours at room temperature. After the solution has been concentrated, the volatile components are removed under reduced pressure at 40° C./0.3 mbar. There is obtained 4.8 parts of 2-(1-methoxy-2-chloroethoxy)-phenyl-N-methyl-N-trimethylsilyl-carbamate (active ingredient no. 1).

The following carbamates, for instance, may be prepared analogously:

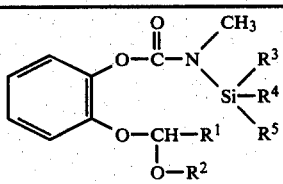

| No. | R$^1$ | R$^2$ | R$^3$ | R$^4$ | R$^5$ |
|---|---|---|---|---|---|
| 2 | CH$_3$ | CH$_3$ | CH$_3$ | CH$_3$ | CH$_3$ |
| 3 | CH$_3$ | C$_2$H$_5$ | CH$_3$ | CH$_3$ | CH$_3$ |
| 4 | CH$_2$Cl | CH$_3$ | CH$_3$ | CH$_3$ | C$_2$H$_5$ |
| 5 | CH$_2$Cl | CH$_3$ | CH$_3$ | C$_2$H$_5$ | C$_2$H$_5$ |
| 6 | CH$_2$Cl | CH$_3$ | C$_2$H$_5$ | C$_2$H$_5$ | C$_2$H$_5$ |
| 7 | CH$_2$Cl | CH$_3$ | CH$_3$ | CH$_3$ | n-C$_3$H$_7$ |
| 8 | CH$_2$Cl | CH$_3$ | CH$_3$ | n-C$_3$H$_7$ | n-C$_3$H$_7$ |
| 9 | CH$_2$Cl | CH$_3$ | CH$_3$ | CH$_3$ | i-C$_3$H$_7$ |
| 10 | CH$_2$Cl | CH$_3$ | CH$_3$ | i-C$_3$H$_7$ | i-C$_3$H$_7$ |
| 11 | CH$_2$Cl | CH$_3$ | CH$_3$ | CH$_3$ | n-C$_4$H$_9$ |
| 12 | CH$_2$Cl | CH$_3$ | CH$_3$ | CH$_3$ | i-C$_4$H$_9$ |
| 13 | CH$_2$Cl | CH$_3$ | CH$_3$ | CH$_3$ | t-C$_4$H$_9$ |
| 14 | CH$_2$Cl | CH$_3$ | CH$_3$ | CH$_3$ | C$_6$H$_5$ |

The N-methyl-N-silyl-carbamates of the formula I according to the invention are suitable for effectively combating pests from the class of insects, ticks and nematodes.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebrana, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephala, Cheimatobia brumata, Hibernia defoliaria, Bupalus piniarus, Hyphantria cunea, Agrotis segetum, Agrotis ypsilon, Barathra brassicae, Cirphis unipuncta, Prodenia litura, Laphygma exigua, Panolis flammea, Earias insulana, Plusia gamma, Alabama argillacea, Lymantria dispar., Lymantria monocha, Pieris brassicae,* and *Aporia crataegi;*

Examples from the Coleoptera order are *Blitophaga undata, Melanotus communis, Limonius californicus, Agriotes lineatus, Agricotes obscurus, Agrilus sinuatus, Meligethes aeneus, Atomaria linearis, Epilachna varivestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;*

Examples from the Diptera order are *Lycoria pectoralis, Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoscyami, Anopheles maculipennis, Culex pipiens, Aedes aegypti, Aedes vexans, Tabanus bovinus, Tipula paludosa, Musca domestica, Fannia canicularis, Muscina stabulans, Glossina morsitans, Oestrus ocis, Chrysomya macellaria, Chrysomya hominivorax, Lucilia cuprina, Lucilia sericata* and *Hypoderma lineata;*

Examples from the Hymenoptera order are *Athalia rosae, Haplocampa minuta, Monomorium pharaonis, Solenopsis geminata,* and *Atta sexdens;*

Examples from the Heteroptera order are *Nezara viridula, Eurygaster integriceps, Blissus leucopterus, Dysdercus cingulatus, Dysdercus intermedius, Piesma quadrata,* and *Lygus pratensis;*

Examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;*

Examples from the Isoptera order are *Reticulitermes lucifugus, Calotermes flavicollis, Leucotermes flavipes* and *Termes natalensis;*

Examples from the Orthoptera order are *Forficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femur-rubrum, Blatta orientalis, Blattella germanica, Periplaneta americana,* and *Blabera gigantea.*

Examples of mites and ticks (Acarina) belonging to the Arachnida class are *Tetranychus telarius, Tetranychus atlanticus, Tetranychus pacificus, Paratetranychus pilosus, Bryobia praetiosa, Ixodes ricinus, Ornithodorus moubata, Ablyomma americanum, Dermacentor silvarum,* and *Boophilus microplus.*

Examples from the Nemathelminthes class are root-knot nematodes, e.g., *Meloidogyne incognita, Meloidogyne hapla,* and *Meloidogyne javanica,* cyst-forming nematodes, e.g., *Heterodera rostochiensis, Heterodera schachtii, Heterodera avenae, Heterodera glycines,* and *Heterodera trifolii,* and stem and leaf eelworms, e.g., *Ditylenchus dipsaci, Ditylenchus destructor, Pratylenchus neglectus, Pratylenchus penetrans, Pratylenchus goodeyi, Paratylen-*

*chus curvitatus* and *Tylenchorhynchus dubius, Tylenchorhynchus claytoni, Rotylenchus robustus, Heliocotylenchus multicinctus, Radopholus similis, Belonolaimus longicaudatus, Longidorus elongatus,* and *Trichodorus primitivus*.

The compounds according to the invention may be successfully employed as pesticides for crop protection, and in the hygiene, stores protection and veterinary sectors.

The active ingredients may be applied as such, in the form of formulations, or of ready-to use application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, andureas, and vegetable products such as grain flours, bark meal, wood meal, and nutshell meal, cellulosic powders, etc.

The formulations contain from 0.1 to 95, and preferably 0.5 to 90, % by weight of active ingredient.

The amount of active ingredient in the ready-to-use formulations may vary within a wide range; it is generally from 0.0001 to 10%, preferably from 0.01 to 1%.

Examples of formulations are given below.

I. 3 parts by weight of 2-(1-methoxy-2-chloroethoxy)-phenyl-N-methyl-N-trimethylsilyl-carbamate is intimately mixed with 97 parts by weight of particulate kaolin. A dust is obtained containing 3% by weight of the active ingredient.

II. 30 parts by weight of 2-(1-methoxy-2-chloroethoxy)-phenyl-N-methyl-N-trimethylsilyl-carbamate is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 20 parts by weight of 2-(1-methoxy-2-chloroethoxy)-phenyl-N-methyl-N-trimethylsilyl-carbamate is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

IV. 20 parts by weight of 2-(1-methoxy-2-chloroethoxy)-phenyl-N-methyl-N-trimethylsilyl-carbamate is dissolved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

The active ingredients may also be successfully used in the ultra-low volume method, where it is possible to apply formulations containing more than 95% of active ingredient, or even the 100% active ingredient.

There may be added to the individual active ingredients (if desired, immediately before use (tankmix)) oils of various types, herbicides, fungicides, other insecticides and bactericides. These agents may be added to the active ingredients according to the invention in a weight ratio of from 1:10 to 10:1.

Examples of active ingredients which may be admixed are as follows: 1,2-dibromo-3-chloropropane, 1,3-dichloropropene, 1,3-dichloropropene+1,2-dichloropropane, 1,2-dibromoethane, 2-sec-butyl-phenyl-N-methylcarbamate, o-chlorophenyl-N-methylcarbamate, 3-isopropyl-5-methylphenyl-N-methylcarbamate, o-isopropoxyphenyl-N-methylcarbamate, 3,5-dimethyl-4-methylmercaptophenyl-N-methylcarbamate, 4-dimethylamino-3,5-xylyl-N-methylcarbamate, 2-(1,3-dioxolan-2-yl)-phenyl-N-methylcarbamate, 1-naphthyl-N-methylcarbamate, 2,3-dihydro-2,2-dimethylbenzofuran-7-yl-N-methylcarbamate, 2,2-dimethyl-1,3-benzodioxol-4-yl-N-methylcarbamate, 2-dimethylamino-5,6-dimethyl-4-pyrimidinyldimethylcarbamate, 2-methyl-2-(methylthio)-propionaldehyde-O-(methylcarbamoyl)-oxime, S-methyl-N-[(methylcarbamoyl)-oxy]-thioacetimidate, methyl-N',N'-dimethyl-N-[(methylcarbamoyl)-oxy]-1-thiooxamidate, N-(2-methyl-4-chlorophenyl)-N'N'-dimethylformamidine, tetrachlorothiophene, 1-(2,6-difluorobenzyl)-3-(4-chlorophenyl)-urea, O,O-dimethyl-O-(p-nitrophenyl)-phosphorothioate, O,O-diethyl-O-(p-nitrophenyl)-phosphorothioate, O-ethyl-O-(p-nitrophenyl)-phenyl-phosphonothioate, O,O-dimethyl-O-(3-methyl-4-nitrophenyl)-phosphorothioate, O,O-diethyl-O-(2,4-dichlorophenyl)-phosphorothioate, O-ethyl-O-(2,4-dichlorophenyl)-phenylphosphonothioate, O,O-dimethyl-O-(2,4,5-trichlorophenyl)-phosphorothioate, O-ethyl-O-(2,4,5-trichlorophenyl)-ethyl-phosphonothioate, O,O-dimethyl-O-(4-bromo-2,5-dichlorophenyl)-phosphorothioate, O,O-dimethyl-O-(2,5-dichloro-4-iodophenyl)-phosphorothioate, O,O-dimethyl-O-(3-methyl-4-methylthiophenyl)-phosphorothioate, O-ethyl-O-(3-methyl-4-methylthiophenyl)-isopropylphosphoramidate, O,O-diethyl-O-[p-(methylsulfynyl)-phenyl]-phosphorothioate, O-ethyl-S-phenylethyl-phosphonodithioate, O,O-diethyl-[2-chloro-1-(2,4-dichlorophenyl)-vinyl]-phosphate, O,O-dimethyl-[2-chloro-1-(2,4,5-trichlorophenyl)]-vinylphosphate, O,O-dimethyl-S-(1-phenyl)-ethylacetate phosphorodithioate, bis-(dimethylamino)-fluorophosphine oxide, octamethyl-pyrophosphoramide, O,O,O,O-tetraethyldithiopyrophosphate, S-chloromethyl-O,O-diethylphosphorodithioate, O-ethyl-S,S-dipropyl-phosphorodithioate, O,O-dimethyl-O-2,2-dichlorovinylphosphate, O,O-dimethyl-1,2-dibromo-2,2-dichloroethylphosphate, O,O-dimethyl-2,2,2-trichloro-1-hydroxyethylphosphonate, O,O-dimethyl-S-[1,2-biscarbethoxyethyl-(1)]-phosphorodithioate, O,O-dimethyl-O-(1-methyl-2-carbomethoxyvinyl)-phosphate, O,O-dimethyl-S-(N-methylcarbamoylmethyl)-phosphorodithioate, O,O-dimethyl-S-(N-methylcarbamoylmethyl)-phosphorothioate, O,O-dimethyl-S-(N-methoxyethylcarbamoylmethyl)-phosphorodithioate, O,O-dimethyl-S-(N-formyl-N-methylcarbamoylmethyl)-phosphorodithioate, O,O-dimethyl-O-[1-methyl-2-(methylcarbamoyl)-vinyl]-phosphate, O,O-dimethyl-O-[(1-methyl-2-dimethylcarbamoyl)-vinyl]-phosphate, O,O-dimethyl-O-[ (1-methyl-2-chloro-2-diethylcarbamoyl)-vinyl]-phosphate, O,O-diethyl-S-(ethylthiomethyl)-phosphorodithioate, O,O-diethyl-S-[(p-chlorophenylthio)-methyl]-phosphorodithioate, O,O-dimethyl-S-(2-ethylthioethyl)-phosphorothioate, O,O-dimethyl-S-(2-ethylthioethyl)-phosphorodithioate, O,O-dimethylsulfynylethyl)-phosphorothioate, O,O-diethyl-S-(2-ethylthioethyl)-phosphorodithioate, O,O-diethyl-S-(2-ethylsulfynylethyl)-phosphorothioate, O,O-diethylthiophosphoryliminophenyl-acetonitrile, O,O-diethyl-S-(2-chloro-1-phthalimidoethyl)-phosphorodithioate, O,O-diethyl-S-[6-chlorobenzoxazolon-(2)-yl-(3)]-methyldithiophosphate, O,O-dimethyl-S-[2-methoxy-1,3,4-thiadiazol-5-onyl-(4)-methyl]-phosphorodithioate, O,O-diethyl-O-[3,5,6-trichloropyridyl-(2)]-phosphorothioate, O,O-diethyl-O-(2-pyrazinyl)-phosphorothioate, O,O-diethyl-O-[2-isopropyl-4-methylpyrimidinyl-(6)]-phosphorothioate, O,O-diethyl-O-[2-(diethylamino)-6-methyl-4-pyrimidinyl]-thionophosphate, O,O-dimethyl-S-(4-oxo-1,2,3-benzotriazin-3-[4H]-yl-methyl)-phosphorodithioate, O,O-dimethyl-S-[(4,6-diamino-1,3,5-triazin-2-yl)-methyl]-phosphorodithioate, O,O-diethyl-(1-phenyl-1,2,4-triazol-3-yl)-thionophosphate, O,S-dimethylphosphoroamidothioate, O,S-dimethyl-N-acetylphosphoramidothioate, α-hexachlorocyclohexane, 1,1-di-(p-methoxyphenyl)-2,2,2-trichloroethane, 6,7,8,9,10,10-hexachloro-1,5,5a,6,9,9a-hexahydro-6,9-methano-2,4,3-benzodioxathiepine-3-oxide, pyrethrins, DL-2-allyl-3-methyl-cyclopenten-(2)-on-(1)-yl-(4)-DL-cis,trans-chrysanthemate, 5-benzylfuryl-(3)-methyl-DL-cis,trans-chrysanthemate, 3-phenoxybenzyl(±)-cis,trans-2,2-dimethyl-3-(2,2-dichlorovinyl)-cyclopropanecarboxylate, α-cyano-3-phenoxybenzyl(±)-cis,trans-2,2-dimethyl-3-(2,2-dichlorovinyl)-cyclopropane carboxylate, (s)-α-cyano-3-phenoxybenzyl-cis(1R,3R)-2,2-dimethyl-3-(2,2-dibromovinyl)-cyclopropane carboxylate, 3,4,5,6-tetrahydrophthalimidoethyl-DL-cis,trans-chrysanthemate, 2-methyl-5-(2-propynyl)-3-furylmethyl-chrysanthemate, and α-cyano-3-phenoxybenzyl-α-isopropyl-4-chlorophenylacetate.

The following examples illustrate the biological action of the new compounds. The comparative agents is the prior art compound 1-naphthyl-N-methyl-carbamate (U.S. Pat. No. 2,903,478).

EXAMPLE A

Contact action on cockroaches (*Blatta orientalis*)

The bottom of 1-liter preserving jars is treated with acetonic solutions of the active ingredients. After the solvents has evaporated, 5 adult cockroaches are placed in each jar, and the kill rate is determined after 48 hours.

| Active ingredient no. | Amount of active ingredient per jar (mg) | Kill rate (%) |
| --- | --- | --- |
| 1 | 0.01 | 80 |
| Comparative agent | 0.1 | 100 |
|  | 0.05 | 20 |

EXAMPLE B

Contact action on granary weevils (*Sitophilus granarius*)

Petri dishes 10 cm in diameter are lined with acetonic solutions of the active ingredients. After the solvent has evaporated, 100 granary weevils are placed in each dish.

After 4 hours, the weevils are transferred to untreated vessels. The kill rate is determined after 24 hours, by counting how many weevils are, after this period has elapsed, capable of leaving an untreated cardboard dish (40 mm in diameter, 10 mm high) within 60 minutes.

| Active ingredient no. | Amount of active ingredient per dish (mg) | Kill rate (%) |
| --- | --- | --- |
| 1 | 0.4 | 100 |
|  | 0.2 | 80 |
| Comparative agent | 2.0 | ineffective |

EXAMPLE C

Continuous contact action on houseflies (*Musca domestica*)

Both covers and bottoms of Petri dishes 10 cm in diameter are lined with a total per dish of 2 ml of acetonic solutions of the active ingredients. After the solvent has evaporated (about 30 mins.), 10 flies are introduced into each dish. The kill rate is determined after 4 hours.

| Active ingredient no. | Amount of active ingredient per dish (mg) | Kill rate (%) |
|---|---|---|
| 1 | 0.02 | 100 |
| Comparative agent | 0.2 | ineffective |

EXAMPLE D

Contact action on aphids (*Aphis fabae*); spray experiment

Potted bean plants (*Vicia faba*) with extensive bean aphid colonies are sprayed to runoff in a spray both with aqueous formulations of the active ingredients. The action is assessed after 48 hours.

| Active ingredient no. | Active ingredient concentration in formulation (wt %) | Kill rate (%) |
|---|---|---|
| 1 | 0.01 | 100 |
| Comparative agent | 0.04 | 100 |
| | 0.02 | ineffective |

EXAMPLE E

Systemic action on bean aphids (*Aphis fabae*); persistence in the soil

Each active ingredient is intimately mixed with 4 kg of garden soil, which is then filled into Mitscherlich pots (diameter 20 cm, height 18 cm). 4 beans (*Vicia faba*) are then planted in each pot at the recommended intervals. When the bean plants are in the 4-leaf stage they are infected with bean aphids. The kill rate or colony formation is registered after 48 hours.

| Active ingredient no. | Active ingredient concentration in soil (wt %) | Kill rate (%) |
|---|---|---|
| 1 | 0.05 | 100 |
| Comparative agent | 0.1 | ineffective |

EXAMPLE F

Contact action on ticks (*Ornithodorus moubata*)

Ticks in the 3rd larval stage are placed in paper bags and dipped for 3 seconds in the emulsion under investigation. The bags are then suspended. The action on the ticks is assessed after 48 hours. When the emulsion contains 0.002 wt% of active ingredient no. 1, the kill rate is 80%.

We claim:

1. An N-methyl-N-silyl-carbamate of the formula

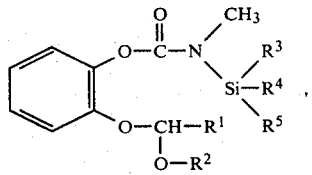

where $R^1$ is chloromethyl, $R^2$ is methyl or ethyl; $R^3$ is methyl or ethyl; $R^4$ is methyl, ethyl or propyl and $R^5$ is methyl, ethyl, propyl, butyl or phenyl.

2. 2-(1-Methoxy-2-chloroethoxy)-phenyl-N-methyl-N-trimethylsilyl-carbamate.

3. A process for combating pests, wherein a pesticidally effective amount of an N-methyl-N-silyl-carbamate as claimed in claim 1 is allowed to act on the pests or their habitat.

4. A process as claimed in claim 3 wherein said pests are insects, ticks or nemotodes.

5. A pesticide comprising pesticidally inactive, inert additives in admixture with an insecticidally effective amount of an N-methyl-N-silyl-carbamate as claimed in claim 1.

6. A pesticide comprising pesticidally inactive, inert additives in admixture with 0.5 to 90% by weight of an N-methyl-N-silyl-carbamate as claimed in claim 1.

7. A compound of the formula I of claim 1 wherein $R^1$ is chloromethyl and $R^2$, $R^3$, $R^4$ and $R^5$ are methyl or ethyl.

* * * * *